United States Patent
Bernardini et al.

(10) Patent No.: US 8,575,066 B2
(45) Date of Patent: Nov. 5, 2013

(54) PROCESS FOR PREPARING AMMONIC GLYPHOSATE GRANULES

(75) Inventors: Marco Bernardini, Lodi (IT); Francesca Borgo, Milan (IT); Luigi Capuzzi, Novara (IT); Edoardo Russo, Piacenza (IT)

(73) Assignee: Sipcam S.p.A., Milan (IT)

( * ) Notice: Subject to any disclaimer, the term of this patent is extended or adjusted under 35 U.S.C. 154(b) by 0 days.

(21) Appl. No.: 13/432,975

(22) Filed: Mar. 28, 2012

(65) Prior Publication Data

US 2012/0190550 A1  Jul. 26, 2012

Related U.S. Application Data

(63) Continuation of application No. 11/920,703, filed as application No. PCT/EP2006/004875 on May 23, 2006, now abandoned.

(30) Foreign Application Priority Data

Jun. 17, 2005 (IT) .............................. MI2005A1138

(51) Int. Cl.
*A01N 57/18* (2006.01)
*B29B 9/00* (2006.01)

(52) U.S. Cl.
USPC ............................................ 504/206; 264/13

(58) Field of Classification Search
USPC ......................................................... 264/13
See application file for complete search history.

(56) References Cited

U.S. PATENT DOCUMENTS

| 2,868,688 A | * | 1/1959 | Benesi et al. | ................. 514/475 |
| 5,388,772 A | * | 2/1995 | Tsau | ................................. 241/17 |
| 5,716,903 A | | 2/1998 | Kramer et al. | |
| 6,228,807 B1 | * | 5/2001 | Kuchikata et al. | ............ 504/206 |
| 6,752,943 B1 | * | 6/2004 | Jadhav et al. | ................. 264/115 |
| 2004/0102323 A1 | | 5/2004 | Vigil et al. | |

FOREIGN PATENT DOCUMENTS

| EP | 0 582 561 A | 2/1994 |
| WO | WO 96/40697 A | 12/1996 |
| WO | WO 01/08480 A | 2/2001 |
| WO | WO 01/08492 A | 2/2001 |
| WO | WO 2004/019684 A | 3/2004 |

* cited by examiner

*Primary Examiner* — Gina C Justice
*Assistant Examiner* — Michael B Pallay
(74) *Attorney, Agent, or Firm* — Arent Fox LLP

(57) ABSTRACT

A process for preparing water-soluble granules of amnionic glyphosate comprising: a) addition of glyphosate acid to a Broensted base which supplies ammonium ions in a molar ratio base/acid comprised between 0.8 and 1.1; b) homogenization of the mixture prepared in a); c) addition of one or more surfactants in amounts in the range 5%-50% by weight based on the glyphosate acid; d) mixing of the mass prepared in c) for a time lower than about 10 minutes until obtaining an extrudable mass; e) extrusion of the mass obtained in d); f) drying until obtaining a granule having a residual moisture lower than 1%.

13 Claims, No Drawings

PROCESS FOR PREPARING AMMONIC GLYPHOSATE GRANULES

CROSS-REFERENCE TO RELATED APPLICATION

This application is a Continuation Application of U.S. patent application Ser. No. 11/920,703, having a filing date of Nov. 19, 2007; which is a National Stage Entry of International Application No. PCT/EP2006/004875, having an international filing date of May 23, 2006; which claims priority to Italian Application No. MI2005A001138, having a filing date of Jun. 17, 2005; the disclosure of each of which is hereby incorporated in its entirety by reference.

The present invention relates to a process for preparing water-soluble granules ammonic glyphosate-based to be used in the agrochemical field.

The glyphosate (N-phosphonmethyl glycine) is well known in the prior art as a compound having an herbicide activity effective for the weed control. It is also known that the glyphosate, being an organic acid not soluble in water, must be converted into its salts to allow the use thereof. The most commonly used salts are the isopropylamine salt, sodic salt and ammonic salt. The isopropylamine salt is formulated and marketed under the form of concentrated aqueous solution. However the need to save money in the manufacturing, transportation and packing disposal costs has recently brought to consider solid formulations, in particular under the form of granules.

The sodic salt and the ammonic salt are particularly suitable to water-soluble granules formulation, more particularly the ammonic glyphosate as less hygroscopic and thus more resistant in moist environment and besides more effective from the biological point of view.

With the ammonic glyphosate term it is meant the glyphosate monoammonic salt.

The water-soluble glyphosate granules can be prepared with various processes.

For example, a known process comprises the salification step of the glyphosate acid with a base, optional addition of other coformulating agents as surfactants, inert agents, antifoam agents and a subsequent granulation step by known techniques in the art as extrusion, agglomeration, preferably extrusion (see for example U.S. Pat. No. 5,633,397).

Another process comprises the mixing step of the glyphosate acid, of the base, of the optional coformulating agents, and the salification step in an extruder (see for example U.S. Pat. No. 5,070,197).

Another process describes the mixing under anhydrous conditions of the glyphosate acid in powder form with a suitable solid base, for example sodium acetate, with no salification reaction; the latter taking place only when the granule is poured into water before the use (see for example WO 92/12,637).

The salification of the glyphosate acid, when required, can be carried out with various methods. In particular the ammonic glyphosate can be prepared by using anhydrous or aqueous solution ammonia, as salification base, by using processes comprising mixing, reaction and extrusion in a single step (see for example U.S. Pat. No. 5,070,197), or processes including separate steps (see for example U.S. Pat. No. 5,633,397 and U.S. Pat. No. 6,734,142).

The processes using ammonia, show the advantage of being carried out in a continuous way due to the high reaction rate solid-gas and solid-liquid. However they suffer the following drawbacks. The anhydrous ammonia is a toxic gas whose use in safety conditions requires specific precautions not usually available in agrodrug formulation plants. The ammonia in aqueous solution is corrosive and also difficult to be safely handled. In both cases the salification by using ammonia results to be strongly exothermic. For these reasons expensive technical precautions in the plant for the process management and for the operator safety must be foreseen as, for example, temperature controls, cooling circuits and safety systems.

A further drawback is noted in single step processes as the equipments required for this kind of process are extruders normally used in the plastic material extrusion, for example high pressure screw extruders, wherein the temperature rises to levels so to make particularly difficult the choice of coformulating agents, in particular of the surfactant. Processes of this kind, requiring the salification in the extruder, have never been described in low pressure extruders usually utilized to produce water soluble or dispersible granules in the agrochemical field. This is likely due to the different configuration and different characteristics of a low pressure extruders compared to high pressure extruders.

The above drawbacks can be overcome by using bases under the solid form, for example ammonium bicarbonate, instead of the ammonia (see for example U.S. Pat. No. 6,228, 807). However these processes show the drawback to require a particularly long preparation step of the mass to be extruded: this step in fact requires the complete salification of the glyphosate acid and this takes place in a time of at least 20-30 minutes. Said characteristic negatively affects the productivity of these processes, a configuration of the salification zone in a continuous way not being achievable. Besides, the salification step can influence the consistence of the mass to be extruded and the incorporation of the surfactant in the formulation.

As known, the surfactants have the purpose to favour, at the time of the use, the glyphosate herbicide effectiveness by acting on the permanence of the drop on leaves, on the adhesion of said drops to the leaf surface and on the penetration of the active principle through the cuticle.

It is desirable that in the final formulation the surfactant, acting as an adjuvant, is present in amounts in the range 5%-35% by weight with respect to the glyphosate, expressed in equivalent acid. However an easy incorporation of high amounts of surfactant only takes place when the formulations have a low glyphosate content. On the other hand, in order to decreasing the manufacturing, the granule transportation and the packing disposal costs, solid products are required more concentrated in glyphosate, making more difficult the incorporation of high amounts of surfactant. As a matter of fact a high concentration of surfactant is hardly adsorbed/absorbed by the mass containing glyphosate, making the processing thereof difficult, especially in case of low pressure extrusion.

Processes preparing ammonic glyphosate capable of containing high surfactant amounts are known. However these processes use anhydrous ammonia (see for example U.S. Pat. No. 5,633,397) or ammonia in aqueous solution (see for example U.S. Pat. No. 6,605,568 and U.S. Pat. No. 5,716, 903) and therefore with the above technical drawbacks.

Processes for preparing granular compositions not requiring the salification step are known. For example WO 92/12, 637 requires the mixing under anhydrous conditions of the glyphosate acid under the powder form with a suitable solid base without any salification reaction takes place which arises only when the granule is poured in water before the use. This process, even though it does not involve any salification step, shows however the drawback of being carried out in a completely anhydrous environment, in case of the soluble glyphosate salts, in order not to cause the salification reaction before the use.

The need was felt to have available a process for preparing ammonic glyphosate granules showing the following combination of properties:
no use of anhydrous ammonia or in aqueous solution;
having a preparation step of the extrudable mass lower than 20 minutes, preferably lower than 10 minutes, and therefore with a high productivity;
carried out also in a continuous way;
allowing to obtain an extrudable mass in low pressure extruders;
capable of incorporating in the granule formulation a high surfactant amount in combination with a high glyphosate amount.

It has surprisingly and unexpectedly found that the preparation of ammonic glyphosate granules with the process described hereinafter allows to solve the above technical problem.

It is therefore an object of the present invention a process for preparing water-soluble ammonic glyphosate granules comprising:
a) addition of glyphosate acid, under the wet cake form, to a solid Broensted base, which supplies ammonium ions, in amounts equal to a molar ratio base/acid between 0.8 and 1.1, preferably between 0.9 and 1.05, optionally in the presence of coformulating agents such as inert, antifoam agents;
b) homogenization of the mixture prepared in a);
c) addition of one or more liquid surfactants, in amounts in the range 5%-50% by weight, preferably 10%-40%, more preferably 12%-35% based on the glyphosate acid;
d) mixing of the mass prepared in c) for a time lower than about 10 minutes, preferably lower than about 5 minutes, more preferably comprised between about 30 seconds and 3 minutes, until obtaining an extrudable mass;
e) extrusion of the mass obtained in d);
f) drying until obtaining a granule having a residual moisture lower than 1%, preferably lower than 0.5%.

In step a) wet cake means that the technical glyphosate acid in powder contains water amounts between 5% and 20%, preferably between 10% and 15%. In general the preferred water amount of the wet cake is such to lead, depending on the used formulation, to an extrudable mass having the consistence of a moist powder in a time lower than 3 minutes when a Ploughshare type mixer, equipped with "chopper" (additional low intensity and high shear strength mixing devices) is used.

In step a) the solid Broensted base supplying ammonium ions can be, for example, selected from ammonium carbonate, bicarbonate, carbamate or mixtures thereof, optionally added of small amounts of antipacking agents as, for example, magnesium carbonate. Preferably the base in step a) is an equimolar mixture of ammonium carbonate, bicarbonate, carbamate. In said solid base, if necessary, lumps, if present, are reduced or removed before adding the other components. Preferably the bicarbonate base is used in admixture with other Broensted bases.

As inert agents to be added in step a), ammonium sulphate, potassium sulphate, sodium sulphate, preferably ammonium sulphate, can be mentioned. Preferably the inert agent is milled before being added to the other components so as to have particle size lower than 500 micron.

As antifoam agents, silicone antifoam agents can preferably be mentioned. The antifoam agent can be added, alternatively, in step c) together with the surfactant.

In step b) mild stirring is generally used, usually for a time lower than one minute.

Homogenization is carried out, for example, in high stirring intensity static mixers of the Ploughshare type, optionally equipped with "choppers" or in continuous mixers having high shear strength. Preferably in this step b) the choppers are not used. Generally, in case of Ploughshare type mixers, mild stirring means that the revolution number is generally between 20 and 40 rpm.

In step c) the surfactant addition is preferably carried out under mild stirring. Stirring can be of the same type (intensity) as that used in step b).

In step c) the surfactant is, for example, selected from solid or liquid compounds at room temperature, for example alkanol amide, betaine derivative, ethoxylated-propoxylated block copolymer, glycerol ester, glycolic ester, imidazoline and its derivatives, lanolin and lecithin derivatives, tertiary and quaternary polyoxyalkylenalkyl amines, polyoxyalkylen alkylkether, polyoxyalkylen alkyl aryl ether, polyoxyalkylen alkyl ester, alkoxylated, and non alkoxylated sorbitan ester, alkyl glycoside, alkyl polyglycoside, alkyl sulphate, alkyl phosphate, sulphonated olefin, alkyl aryl sulphonate, polyoxyalkylen alkyl ether sulphate, polyoxyalkylen alkyl ether phosphate, sulphosuccinate derivative, taurate, vegetable oil sulphonate of a fat acid, of an alcohol, of an alcoholalkoxylate, of a fat acid ester, an aromatic derivative of a fat acid ester or mixtures thereof, amine derivatives of vegetable oils or of fat acids.

Preferably said surfactant is added in a liquid form to the mixture obtained in step b).

Preferably as surfactant ethoxylated tallow amine is used, having general formula

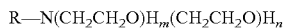

(R=saturated alkyl chain having 16-18 carbon atoms).

Step d) is preferably carried out under stirring with higher intensity than that of step c). In the above Ploughshare type mixers, rates between about 80 and 120 rpm are generally used. Preferably in this step choppers are used.

In step d) the mass mixing preferably takes place in the same device wherein the previous step c) has been carried out but increasing the shear rate so as to obtain an extrudable mass, that is a mass having a consistence suitable to be extruded in the used extruder.

The consistence suitability mainly depends on the technology selected for the granulation: said consistence can range from a moist powder consistence to a dough-like consistence; it is preferable to have a consistence lower than the dough-like consistence.

In the particular case of granulation by low pressure extruders of the so called radial, basket or twin dome type, the suitable consistence is that of a moist powder capable to be plastically deformed when subjected to compression (for example in the hand palm). A suitable extruder to carry out the process of the invention is a low pressure extruder basket type.

Without to be bound to any theory, the Applicant keeps that the optimal conditions to carry out step d) are: mass mixing for a time sufficient to obtain an extrudable mass as defined above.

Generally, by using Ploughshare mixers at the above rates, the extrudable mass can be obtained even with times lower than one minute.

Preferably, during the time wherein step d) takes place, the temperature remains substantially constant.

The mass obtained after the mixing d) is essentially formed of unreacted glyphosate acid, ammonic glyphosate, Broensted base. As a matter of fact the Applicant has unexpectedly and surprisingly found that the completion of the salification reaction is not a necessary condition for obtaining, before, an extrudable mass, and, after, a good granule based on ammonic glyphosate.

The unreacted glyphosate acid is present in the mass obtained in d) preferably in amounts ranging from a maximum of 70% to a minimum of 10% with respect to the initial acid amount. It follows that ammonic glyphosate in a minimum molar amount of 30% and a maximum of 90% with respect to the starting glyphosate acid and the corresponding amount of unreacted base will be present in the extrudable mass.

The presence of unreacted glyphosate acid and thus of unreacted Broensted base in the extrudable mixture is shown from the carbon dioxide development (effervescence) when a portion of the mixture obtained in the mixing step d) is put in water. As said, during step d) the mass temperature substantially remains unchanged.

In step e) the extrusion of the mass obtained in d) is preferably carried out by low pressure extruders and produces strings, which break by fall in coherent and moist granules to be dried. Said granules, when put in water, show gas development.

In step f) drying is preferably carried out in fluid bed dryers, generally at temperatures in the range 70° C.-120° C., preferably 80° C.-100° C. The drying temperature is however such as not to imply degradation or loss of surfactant or of other formulation additives.

The dried granules obtained in step f), when put in water, do not show any gas development but are completely water-soluble without carbon dioxide development and without undissolved sediments. This means that the salification is completed during step f). The drying step generally lasts between 10 and 15 minutes or at any rate for a time such as to obtain a granule having the above characteristics when put in water, and a residual moisture lower than 1%, preferably lower than 0.5%.

The Applicant has found that with the process of the present invention it is possible to prepare water-soluble amnionic glyphosate granules by a simple process, not requiring the use of dangerous substances, not implying heat development, allowing the incorporation in the formulation of high amounts of surfactant. Furthermore the process of the present invention has realization times much lower than those of known processes requiring the salification step. It thus follows a higher productivity, the time and the initial amount of components being equal, besides the possibility to carry out the process of the present invention even in a continuous way.

It has besides been found that with the process of the present invention it is possible to remarkably increase the surfactant content in the granule. As said above, this is a highly desired characteristic for the glyphosate granules.

The granules obtainable with the process of the invention have an equivalent glyphosate acid content higher than or equal to 48% by weight and a surfactant content in the range 5%-25% by weight, preferably 10%-20% by weight.

Preferred compositions are the following (% by weight):

| 1. | pure ammonic glyphosate | 79.2 (equivalent acid 72) |
|---|---|---|
| | surfactant | 10 |
| | inert agents and impurities | to 100 |
| 2. | pure ammonic glyphosate | 79.2 (equivalent acid 72) |
| | surfactant | 15 |
| | inert agents and impurities | to 100 |

-continued

| 3. | pure ammonic glyphosate | 74.8 (equivalent acid 68) |
|---|---|---|
| | surfactant | 15 |
| | inert agents and impurities | to 100 |
| 4. | pure ammonic glyphosate | 66 (equivalent acid 60) |
| | surfactant | 20 |
| | inert agents and impurities | to 100 |

The surfactant preferably used in these compositions is tallow amine.

Some illustrative but not limitative Examples of the present invention follow.

EXAMPLES

Characterization

Determination of the Glyphosate Acid Content in the Granule

It was determined by analytical method CIPAC 284/SG/M by using the HPLC (High Performance Liquid Chromatography) technique with ionic exchange column, wave length UV 195 nm and external standard.

Determination of the pH of the Granule Dissolved in Water

It was determined by CIPAC 75 method by using a common pHmeter.

Determination of the Granule Solubility

The glyphosate granule solubility was determined by the following method.

A granular product amount having a known glyphosate acid content is weighed so as to obtain 100 ml of a solution containing glyphosate acid in concentration 5 times higher than the employment dose (employment dose=14.4 g/l). The aqueous solution is prepared by stirring for two minutes with a glass rod, the product is poured in a 100 ml graduated conical cylinder ASTM D 96. The cylinder is then capped and turned over 15 times in about ½ minute. Then the solution is allowed to rest for 1 hour in a bath at a temperature of 20° C.±2. Then the presence of possible sediments is visually controlled with a ±0.05 ml precision.

Determination of the Residual Moisture Content of the Granule

It was determined by the CIPAC MT 30.1 method.

Example 1

2,348 grams of an equimolar mixture of ammonium carbonate, bicarbonate and carbamate, commercially known as Hartshorn salt (E503) having ammonia titre of 31%, were cleared removed from lumps in a Loedige mixer (of the Ploughshare type) equipped with chopper; 8,297 grams of technical glyphosate having titre 96.9% with respect to the dry product and moisture 10%, 776 grams of ammonium sulphate previously milled by a rung mill were then added and mixed for one minute. While maintaining the mixture under mild stirring, corresponding to 20 rev/minute, 1,000 g of tallow amine (surfactant) Emulson® AG/PE 3SS (corresponding to a content of 10% by weight based on the final composition and of 13% by weight based on the acid) and 10 grams of antifoam agent Antifoam® SL were added.

The obtained mass was then subjected to mixing at the maximum intensity corresponding to 100 rev/minute, with the aid of a chopper for 3 minutes until obtaining an extrudable mixture.

The mixture had the consistence of a moist powder, deformable by compression in a hand.

The mass temperature during said step maintained itself lower than 35° C.

Said mixture was then sent to a low pressure basket extruder having a diameter of 130 mm and a screen with 1 mm thickness and holes, and extruded.

The extruded product was then dried in a fluid bed dryer for 15 minutes with hot air having an inlet temperature of 100° C.

The whole process was monitored by carrying out some solubility test of the mass to be extruded, of the extruded granule and of the dried granule, observing development of carbon dioxide in case of the extrudable mass and of the extruded granule, and not observing development of carbon dioxide in case of the dried granule.

The latter was then characterized by carrying out the analyses described in the characterization, obtaining the following values:
glyphosate acid content: 72% by weight;
pH: 3.9;
solubility: complete without sediments;
residual moisture: 0.5%.

Example 2

The Example 1 was repeated but by using 276 grams of ammonium sulphate previously milled instead of 776 grams.

While maintaining the mixture under mild stirring, corresponding to 20 rev/minute, 1,500 g of tallow amine (surfactant) Emulson® AG/PE 3SS (corresponding to a content of 15% based on the dry product and of 20.8% based on the acid) and 10 grams of antifoam agent Antifoam® SL were added.

The obtained mass was then subjected to mixing at the maximum intensity corresponding to 100 rev/minute, with the aid of a chopper for 3 minutes until obtaining an extrudable mixture.

The mixture had the consistence of a moist powder, deformable by compression in a hand.

The mass temperature during said step maintained itself lower than 35° C.

Said mixture was then sent to the extruder described in the Example 1 and extruded; the extruded product was then dried in the dryer described in the Example 1 under the same conditions.

The whole process was monitored by carrying out some solubility test of the mass to be extruded, of the extruded granule and of the dried granule, observing development of carbon dioxide in case of the mass to be extruded and of the extruded granule, and not observing development of carbon dioxide in case of the dried granule.

The dried granule was then characterized by carrying out the analyses described in the characterization, obtaining the following values:
glyphosate acid content: 72%;
pH: 3.9;
solubility: complete without sediments;
residual moisture: 0.5%.

Example 3

The Example 1 was exactly repeated except that the mixing of step d) was carried out for 1 minute. The mass resulted extrudable as in the Example 1 and the analyses carried out on the dried granule gave the following values:
glyphosate acid content: 72%;
pH: 3.9;
solubility: complete without sediments;
residual moisture: 0.5%.

Example 4

Comparative

The Example 1 was exactly repeated except that the mixing of step d) was carried out for about 30 minutes according to U.S. Pat. No. 6,228,807.
It has been noticed:
a temperature increase up to over 60° C., due to the friction inside the mixer;
the complete salification of the glyphosate acid;
the non extrudability of said mass.

Furthermore also the subsequent cooling of the mass up to room temperature by flowing of water in the jacket, carried out in 30 minutes, has not allowed to obtain an extrudable mass.

Example 5

Comparative

The Example 1 was repeated except that 1,776 grams of ammonium sulphate were used and no surfactant was used.

Mixing was carried out at the maximum intensity, corresponding to 100 rev/minute, with the aid of a chopper for 3 minutes; under these conditions it was not possible to obtain an extrudable mixture.

The mass temperature during said step maintained itself lower than 35° C.

Example 6

Comparative

The Example 1 was repeated but in the absence of inert agent, surfactant and antifoam agent.

The base and the acid were subjected to mixing at the maximum intensity corresponding to 100 rev/minute, with the aid of a chopper for 3 minutes; under these conditions it was not possible to obtain an extrudable mixture.

The mass temperature during said step maintained itself lower than 35° C.

Example 7

Comparative

The Example 1 was repeated but by using 1,476 grams of ammonium sulphate milled as in the Example 1 and 300 g of tallow amine (surfactant) Emulson® AG/PE 3SS (corresponding to a content of 3% with respect to the final composition and of 4.2% with respect to the acid)

The obtained mass was then subjected to mixing at the maximum intensity, corresponding to 100 rev/minute, with the aid of a chopper for 3 minutes.

The obtained mass did not result extrudable in the extruder described in the Example 1.

Example 8

2,257 grams of an equimolar mixture of ammonium carbonate, bicarbonate and carbamate, commercially known as Hartshorn salt (E503) having ammonia titre of 31%, were cleared from lumps in a Loedige mixer (Ploughshare type) equipped with chopper; 7,976 grams of technical glyphosate having titre 96.9% and moisture 10%, 917 grams of ammonium sulphate previously milled by a rung mill were then added and mixed for one minute.

While maintaining the mixture under mild stirring, corresponding to 20 rev/minute, 1,500 g of tallow amine (surfactant) Emulson® AG/PE 3SS (corresponding to a content of 15% based on the final composition and of 22% based on the acid) and 10 grams of antifoam agent Antifoam® SL were added.

The obtained mass was then subjected to mixing at the maximum intensity, corresponding to 100 rev/minute, with the aid of a chopper for 3 minutes until obtaining an extrudable mixture.

The mixture had the consistence of a moist powder, deformable by compression in a hand.

The mass temperature during said step maintained itself lower than 35° C.

Said mixture was then sent to the extruder described in the Example 1 and extruded. The extruded product was then dried in the dryer of the Example 1 and under the same conditions.

The whole process was monitored by carrying out some solubility test of the mass to be extruded, of the extruded granule and of the dried granule, observing development of carbon dioxide in case of the mass to be extruded and of the extruded granule, and not noticing development of carbon dioxide in case of the dried granule.

The dried granule was then characterized by carrying out the analyses described in the characterization, obtaining the following values:
- glyphosate acid content: 68%;
- pH: 3.9;
- solubility: complete without sediments;
- residual moisture: 0.5%.

Example 9

1,957 grams of an equimolar mixture of ammonium carbonate, bicarbonate and carbamate, commercially known as Hartshorn salt (E503) having ammonia titre of 31%, were cleared from lumps in a Loedige mixer (Ploughshare type) equipped with chopper; 6,914 grams of technical glyphosate having titre 96.9% and moisture 10%, 1,145 grams of ammonium sulphate previously milled by a rung mill were then added and mixed for one minute.

While maintaining the mixture under mild stirring, corresponding to 20 rev/minute, 2,000 g of tallow amine (surfactant) Emulson® AG/PE 3SS (corresponding to a content of 20% based on the final composition and of 33.3% based on the acid) and 10 grams of antifoam agent Antifoam® SL were added.

The obtained mass was then subjected to mixing at the maximum intensity, corresponding to 100 rev/minute, with the aid of a chopper for 3 minutes until obtaining an extrudable mixture.

The mixture had the consistence of a wet powder, deformable by compression in a hand.

The mass temperature during said step maintained itself lower than 35° C.

Said mixture was then sent to the extruder described in the Example 1 and extruded; the extruded product was then dried in the dryer of the Example 1 and under the same conditions.

The whole process was monitored by carrying out some solubility tests of the mass to be extruded, of the extruded granule and of the dried granule, observing development of carbon dioxide in case of the mass to be extruded and of the extruded granule, and not noticing development of gas in case of the dried granule.

The dried granule was then characterized by carrying out the analyses described in the characterization, obtaining the following values:
- glyphosate acid content: 60%;
- pH: 3.9;
- solubility: complete without sediments;
- residual moisture: 0.5%.

The obtained granule shows a high concentration of glyphosate acid in combination with a high concentration of surfactant, whose ratio is comparable to that found in commercial products having a lower glyphosate titre, for example granules containing 36% by weight of glyphosate.

The invention claimed is:

1. A process for preparing water-soluble ammonic glyphosate granules comprising:
   a) addition of glyphosate acid, under wet cake form, to a solid Broensted base, which supplies ammonium ions, in amounts equal to a molar ratio base/acid between 0.8 and 1.1, optionally in the presence of coformulating agents;
   b) homogenization of the mixture prepared in a);
   c) addition of one or more surfactants, in a liquid form under stirring in amounts in the range 5%-50% by weight based on the glyphosate acid;
   d) mixing of the mass prepared in c) for a time lower than 10 minutes, until obtaining an extrudable mass wherein unreacted glyphosate acid, ammonium glyphosate and Broensted base are present; wherein, with respect to the initial acid amount, the unreacted glyphosate acid is present in an amount ranging from 70% to 10%, ammonic glyphosate is present a molar amount from 30% to 90%, and the corresponding amount of the unreacted base is present in the extrudable mass;
   e) extrusion by low pressure extruders of radial, basket or twin dome types of the mass obtained in d);
   f) drying until obtaining a granule having a residual moisture lower than 1% and completing salification of glyphosate.

2. A process according to claim 1, wherein the Broensted base of step a) is selected from the group consisting of: ammonium carbonate, bicarbonate, carbamate and mixtures thereof, and wherein antipacking agents are added optionally.

3. A process according to claim 2, wherein the base is an equimolar mixture of ammonium carbonate, bicarbonate, and carbamate.

4. A process according to claim 1, wherein the coformulating agents of step a) are selected from the group consisting of: ammonium sulphate, potassium sulphate, and sodium sulphate.

5. A process according to claim 1, wherein the coformulating agent is a silicone antifoam agent.

6. A process according to claim 1, wherein the step b) takes place under stirring in a mixer working between 20 and 40 rpm.

7. A process according to claim 1, wherein the surfactant addition of step c) takes place under stirring in a mixer working between 20 and 40 rpm.

8. A process according to claim 1, wherein the surfactant is selected from solid or liquid surfactants at room temperature.

9. A process according to claim 1, wherein the mixing in step d) is carried out under stirring in a mixer, optionally equipped with a chopper, working at a rate between about 80 and 120 rpm.

10. A process according to claim 9, wherein the mixer equipped with the chopper is used.

11. A process according to claim 1, wherein the drying of step f) is carried out in fluid bed dryers.

12. A process according to claim 11, wherein the time used for drying ranges from 10 to 15 minutes.

13. The process according to claim 1, wherein the surfactant is selected from the group consisting of: alkanol amide, ethoxylated-propoxylated block copolymer, glycerol ester, glycolic ester, imidazoline, tertiary and quaternary polyoxyalkylenalkyl amines, polyoxyalkylen alkylether, polyoxyalkylen alkyl aryl ether, polyoxyalkylen alkyl ester, alkoxylated and non alkoxylated sorbitan ester, alkyl glycoside, alkyl polyglycoside, alkyl sulphate, alkyl phosphate, sulphonated olefin, alkyl aryl sulphonate, polyoxyalkylen alkyl ether sulphate, polyoxyalkylen alkyl ether phosphate, and taurate.

* * * * *